US010238791B2

(12) United States Patent
Arnholt et al.

(10) Patent No.: US 10,238,791 B2
(45) Date of Patent: Mar. 26, 2019

(54) FLEXIBLE MEMBER FOR RESISTING RETROGRADE FLOW

(71) Applicant: Boston Scientific Scimed, Inc., Maple Grove, MN (US)

(72) Inventors: Devon N. Arnholt, St. Paul, MN (US); Joel T. Eggert, Plymouth, MN (US); Jonathan P. Fettig, Forst Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 456 days.

(21) Appl. No.: 14/988,550

(22) Filed: Jan. 5, 2016

(65) Prior Publication Data
US 2016/0193457 A1 Jul. 7, 2016

Related U.S. Application Data

(60) Provisional application No. 62/099,810, filed on Jan. 5, 2015.

(51) Int. Cl.
*A61M 5/14* (2006.01)
*A61M 25/00* (2006.01)
(Continued)

(52) U.S. Cl.
CPC .......... *A61M 5/14* (2013.01); *A61M 25/0082* (2013.01); *A61F 2/01* (2013.01); *A61M 25/04* (2013.01); *A61M 31/005* (2013.01); *A61M 2025/0004* (2013.01); *A61M 2025/0096* (2013.01); *A61M 2039/2433* (2013.01)

(58) Field of Classification Search
CPC ................ A61M 5/14; A61M 25/0067; A61M 25/0074; A61M 25/0075; A61M 25/0082; A61M 25/04; A61M 31/005; A61M 2025/0004; A61M 2025/0076; A61M 2025/0096; A61M 2025/0175;
(Continued)

(56) References Cited
U.S. PATENT DOCUMENTS 4,921,478 A * 5/1990 Solano ................ A61M 25/104
604/103.07
5,041,093 A * 8/1991 Chu ...................... A61B 17/221
604/104
(Continued)

FOREIGN PATENT DOCUMENTS

WO 2014/150013 9/2014

*Primary Examiner* — Kami A Bosworth

(57) ABSTRACT

The present disclosure is directed to a valve structure that comprises a flexible structure having a distal portion configured for attachment to a first member and a proximal portion configured for attachment to a second member. The flexible structure is configured such that when the first member is extended distally relative to the second member, the flexible structure adopts a reduced width profile and such that when the first member is retracted proximally relative to the second member to a point of maximal retraction, the flexible structure adopts an expanded width profile, which is more resistant to deformation due to fluid pressure in a proximal direction than it is to deformation due to fluid pressure in a distal direction. The present disclosure is also directed to devices and methods pertaining to such a valve structure.

20 Claims, 2 Drawing Sheets

(51) Int. Cl.
    *A61M 39/24*     (2006.01)
    *A61F 2/01*     (2006.01)
    *A61M 25/04*     (2006.01)
    *A61M 31/00*     (2006.01)

(58) Field of Classification Search
    CPC .. A61M 2025/0293; A61M 2025/1052; A61M 2039/2433; A61F 2/01
    See application file for complete search history.

(56) References Cited

U.S. PATENT DOCUMENTS

| | | | |
|---|---|---|---|
| 6,210,370 B1 * | 4/2001 | Chi-Sing | A61B 17/22032 604/104 |
| 6,358,266 B1 * | 3/2002 | Bonutti | A61B 17/0218 600/207 |
| 7,780,696 B2 * | 8/2010 | Daniel | A61B 17/221 606/200 |
| 8,696,699 B2 | 4/2014 | Chomas et al. | |
| 8,986,291 B2 * | 3/2015 | Desai | A61B 17/221 128/898 |
| 2002/0173819 A1 | 11/2002 | Leeflang et al. | |
| 2003/0176884 A1 | 9/2003 | Berrada et al. | |
| 2005/0049577 A1 * | 3/2005 | Snell | A61M 25/0009 604/544 |
| 2007/0149996 A1 | 6/2007 | Coughlin | |
| 2013/0110152 A1 * | 5/2013 | Dubrul | A61B 10/0266 606/194 |
| 2015/0306311 A1 | 10/2015 | Pinchuk et al. | |
| 2018/0271635 A1 * | 9/2018 | Becking | A61B 17/221 |

\* cited by examiner

FLEXIBLE MEMBER FOR RESISTING RETROGRADE FLOW

CROSS-REFERENCE TO RELATED APPLICATIONS

This application claims the benefit of U.S. Provisional Application No. 62/099,810, filed Jan. 5, 2015 and entitled "FLEXIBLE MEMBER FOR RESISTING RETROGRADE FLOW," which is hereby incorporated by reference in its entirety.

BACKGROUND

Off target delivery of therapeutics including drugs and embolic compositions due to retrograde flow can cause unintended side effects as well as result in variable dosing to the target tissue. The present disclosure is directed to devices and methods that address this and other issues.

SUMMARY

In one aspect, the present disclosure provides valve structures that comprise a flexible structure having a distal portion configured for attachment to a first member and a proximal portion configured for attachment to a second member. The flexible structure is configured such that when the first member is extended distally relative to the second member, the flexible structure adopts a reduced width profile and such that when the first member is retracted proximally relative to the second member, for example, to a point of maximum retraction, the flexible structure adopts an expanded width profile that is more resistant to deformation due to fluid pressure in a proximal direction than it is to deformation due to fluid pressure in a distal direction.

In another aspect, the present disclosure provides devices that are configured for insertion in a lumen. The device comprises: (a) an outer elongated member, (b) an inner elongated member disposed within the outer elongated member and axially movable with respect to the outer elongated member, and (c) a flexible structure having a distal portion attached to the inner elongated member and a proximal portion attached to the outer elongated member. The flexible structure is configured such that when the inner elongated member is extended distally relative to the outer elongated member, the flexible structure adopts a reduced width profile and such that when the inner elongated member is retracted proximally relative to the outer elongated member, for example, to a point of maximum retraction, the flexible structure adopts an expanded width profile that is more resistant to deformation due to fluid pressure in a proximal direction than it is to deformation due to fluid pressure in a distal direction.

Such valve structures and devices are advantageous, for example, in that when the flexible structure engages an inner surface of a lumen, a check valve is created, due to the fact that the expanded width profile is more resistant to deformation as a result of fluid pressure in a proximal direction than it is to deformation as a result of fluid pressure in a distal direction.

In various embodiments, which may be used in combination with any of the above aspects, the device may comprise a stop to establish the point of maximal retraction. For instance, the inner elongated member may comprise a stop to establish the point of maximal retraction.

In various embodiments, which may be used in combination with any of the above aspects and embodiments, the flexible structure may have a resting shape having a width that increases from a proximal end of the flexible structure towards a center of the flexible structure. For instance, the resting shape of the flexible structure may comprise a first partial conical, partial pyramidal or partial spheroidal structure which has a width that increases from a proximal end of the flexible structure toward a center of the flexible structure.

In various embodiments, which may be used in combination with any of the above aspects and embodiments, the flexible structure may have a resting shape having a width that decreases from a center of the flexible structure towards a proximal end of the flexible structure. For instance, the resting shape of the flexible structure may comprise a second partial conical, partial pyramidal or partial spheroidal structure which has a width that decreases from a center of the flexible structure toward a proximal end of the flexible structure.

In various embodiments, which may be used in combination with any of the above aspects and embodiments, the proximal portion of the flexible structure may comprise (a) a free proximal portion and (b) an attached proximal portion that is attached to the outer elongated member, and the distal portion of the flexible structure may comprise (a) a free distal portion and (b) an attached distal portion that is attached to the inner elongated member.

In various embodiments, which may be used in combination with any of the above aspects and embodiments, when the inner elongated member is at the point of maximal retraction, the flexible member may have a free proximal portion with a width that increases in a proximal-to-distal direction. For example, the free proximal portion may comprise a first partial conical, partial pyramidal or partial spheroidal structure which has a width that increases in a proximal-to-distal direction.

In various embodiments, which may be used in combination with any of the above aspects and embodiments, the flexible member may have a free distal portion whose resting shape is such that the free distal portion comprises a second partial conical, partial pyramidal, or partial spheroidal structure which has a width that increases in a distal-to-proximal direction. In some instances, the upon retraction of the inner elongated member proximally relative to the outer elongated member, the second partial conical, partial pyramidal or partial spheroidal structure at least partially inverts and at least partially nests within the first partial conical, partial pyramidal or partial spheroidal structure.

In various embodiments, which may be used in combination with any of the above aspects and embodiments, the flexible member may have a free proximal portion that comprises a first conical frustum; or the flexible member may have a free distal portion that comprises a second conical frustum; or the flexible member may have a free proximal portion that comprises a first conical frustum and a free distal portion that comprises a second conical frustum.

In some of these embodiments, the flexible member may have a resting shape in which a width of the second conical frustum increases in a distal-to-proximal direction. Alternatively or in addition, in some of these embodiments, when the inner elongated member is retracted to the point of maximal retraction, the second conical frustum may have a configuration in which the width of the second conical frustum increases in a proximal-to-distal direction and in which the second conical frustum is at least partially nested within the first conical frustum. Alternatively or in addition, in some of these embodiments, the second conical frustum may be thinner than the first conical frustum thereby rendering the second conical frustum more flexible than the first conical frustum. Alternatively or in addition, in some of these embodiments, the second conical frustum may be provided with a plurality of apertures thereby rendering the second conical frustum more flexible than the first conical frustum. For example, the apertures in the distal portion may form a plurality of elongated members that are positioned between fixed distal portion and the free proximal portion, among other possibilities.

In various embodiments, which may be used in combination with any of the above aspects and embodiments, the device may be a catheter.

Other aspects of the disclosure pertain to methods comprising (a) inserting a device in accordance any of the above aspects and embodiments into a lumen while the flexible structure is in the reduced width profile and (b) retracting the inner elongated member proximally relative to the outer elongated member to the point of maximal retraction, at which point the flexible structure adopts the expanded width profile and engages an inner surface of the lumen, thereby creating a check valve in which the expanded width profile is more resistant to deformation due to fluid pressure in the proximal direction than it is to deformation due to fluid pressure in the distal direction. In certain instances, the lumen may be a blood vessel and the device may be a catheter, in which case a therapeutic agent may be delivered from the catheter at a point that is distal to the flexible member.

These and other aspects, embodiments and advantages of the present invention will become immediately apparent to those of ordinary skill in the art upon review of the detailed description and claims to follow.

DETAILED DESCRIPTION

As previously noted, off target delivery of therapeutic agents including drugs and embolic compositions as a result of retrograde blood flow can cause unintended side effects and also result in variable dosing to the target tissue. While a device that occludes blood flow can be used to address the retrograde flow, such an occlusive device can also have the unintended consequence of preventing or delaying the therapeutic agent from arriving at the target tissue site due to lack of blood flow to carry it forward.

The present disclosure is directed to flexible structures that act as valve components and to catheters comprising such flexible structures, which can significantly limit retrograde flow while at the same time allowing for normal blood flow.

In one aspect, the present disclosure provides a catheter which comprises an outer elongated member, an inner elongated member, which is disposed within the outer elongated member and axially movable with respect to the outer elongated member, and a flexible structure, which has a distal portion attached to the inner elongated member and a proximal portion attached to the outer elongated member such that when the inner elongated member is extended distally relative to the outer elongated member the structure adopts a reduced diameter profile and such that when the inner elongated member is retracted proximally relative to the outer elongated member the structure adopts an expanded diameter profile. Moreover, engagement of the flexible structure with a wall of a surrounding fluid vessel upon adopting the expanded diameter profile creates a check valve for fluid flowing in the fluid vessel. In particular, a check valve is formed wherein fluid flow in a distal-to-proximal direction is at least substantially blocked relative to fluid flow in a proximal-to-distal direction.

Figure 1A:
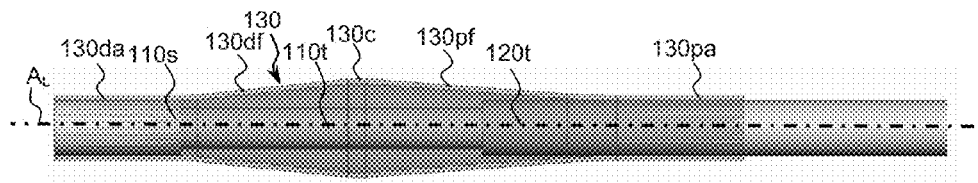
FIGS. 1A-1C are schematic longitudinal views of a catheter in accordance with an embodiment of the present disclosure.
Figure 1B:
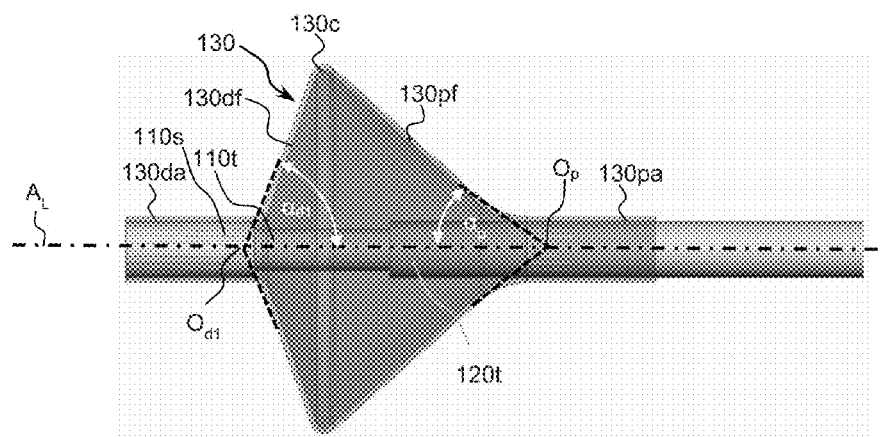
Figure 1C:
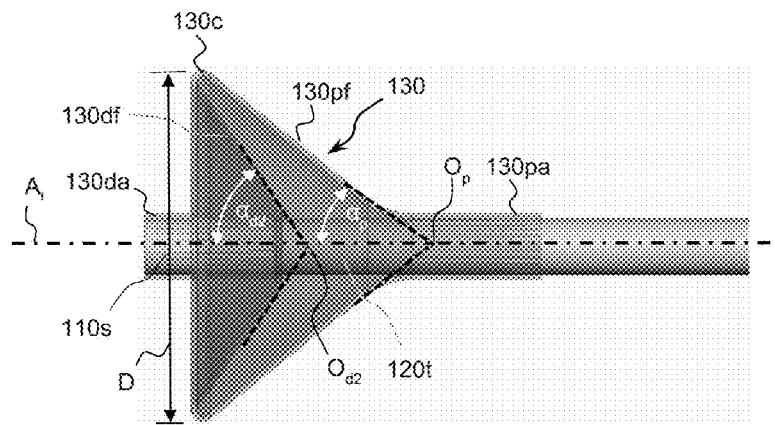

Turning now to FIGS. 1A-1C, a flexible structure 130 in accordance with an embodiment of the present disclosure is shown, which includes a proximal portion comprising a free proximal portion 130 pf and an attached proximal portion 130 pa that is attached to an elongated member comprising an outer tubular member 120 t. The flexible structure 130 further includes a distal portion comprising a free distal portion 130 df and an attached distal portion 130 da that is attached to an elongated member that comprises an inner tubular member 110 t and a stop member 110 s. The free proximal portion 130 pf and free distal portion 130 df are connected by a narrow central portion 130 c. The flexible structure 130 illustrated is symmetric about a longitudinal axis $A_L$. The inner tubular member 110 t is disposed within the outer tubular member 120 t and runs the length of the outer tubular member 120 t. As seen from FIG. 1A, when the inner tubular member 110 t is pushed distally relative to the outer tubular member 120 t the flexible structure 130 adopts a low profile (i.e., reduced diameter) configuration.

When an operator begins to pull the inner tubular member 110t proximally relative to the outer tubular member 120t, the flexible structure 130 increases in overall diameter as shown in FIG. 1B. In the embodiment shown in FIG. 1B, the inner tubular member 110t has been proximally withdrawn to a position where the flexible structure assumes its approximate resting shape (i.e., the shape the flexible structure takes when free of external forces). Typically, at least the free proximal portion 130pf of the flexible structure 130 is molded (all of the flexible structure 130 is molded in various embodiments), in which case the resting shape is the as-molded shape.

In preferred embodiments, the free proximal portion 130pf of the flexible structure 130 has a resting shape that comprises a partial conical, partial pyramidal or partial spheroidal structure which increases in width toward a center of the flexible structure 130.

In the particular embodiment shown, the free proximal portion 130pf forms a partial conical structure having an origin $O_p$ (shown by intersection of dashed imaginary lines) that lies proximal to the free proximal portion 130pf, specifically, the free proximal portion 130pf comprises a conical frustum having an origin $O_p$ that lies proximal to the frustum.

In some embodiments, the free distal portion 130df of the flexible structure 130 also has a resting shape that comprises a partial conical, partial pyramidal or partial spheroidal structure which increases in width toward a center of the flexible structure 130. In these embodiment, at least the free distal portion 130df of the flexible structure 130 may be molded, in which case the resting shape is the as-molded shape.

In the particular embodiment shown, the free distal portion 130df forms a partial conical structure having an origin $O_{d1}$ (shown by intersection of dashed imaginary lines) that lies distal to the free distal portion 130df, specifically, the free distal portion 130*df* comprises a frustum of a cone having an origin $O_n$ that lies proximal to the frustum.

Angles $\alpha_{d1}$ and $\alpha_p$ are the angles between the longitudinal axis $A_l$ and the surfaces of the distal partial conical structure and the proximal partial conical structure, respectively. Values for $\alpha_{d1}$ and $\alpha_p$ range between 0 and 90°, i.e., ranging from 0° to 10° to 20° to 30° to 40° to 50° to 60° to 70° to 80° to 90° (i.e., ranging between any two of the preceding numerical values). Typical values for $\alpha_{d1}$ range between 5° and 85°, more typically between 60° and 80°. Typical values for $\alpha_p$ range between 10° and 80°, more typically between 30° and 60°.

Alternatively, as noted above, the free proximal portion 130*pf* may form a partial spheroidal structure (e.g., partial sphere, partial oblate spheroid, partial prolate spheroid, etc.) or may form a partial pyramidal structure (e.g., a pyramid having a polygonal base with 3, 4, 5, 6, 7, 8, 9, 10 or more sides, with the base approaching the shape of a circle with an increasing number of sides for a regular polygon) and having an origin $O_p$ proximal to the free proximal portion 130*pf*, for example, forming a hemisphere or forming a frustum of a pyramid having an origin $O_p$ proximal to the frustum, among other possibilities. Similarly, the free distal portion 130*df* may form a partial spheroidal structure (e.g., partial sphere, partial oblate spheroid, partial prolate spheroid, etc.) or may form a partial pyramidal structure (e.g., having a polygonal base with 3, 4, 5, 6, 7, 8, 9, 10 or more sides) having an origin $O_{d1}$ distal to the free distal portion 130*df*, for example, forming a hemisphere or forming a frustum of a pyramid having an origin $O_{d1}$ distal to the frustum, among other possibilities.

Turning now to FIG. 1C, as the operator continues to pull the inner tubular member 110*t* proximally relative to the outer tubular member 120*t*, the free distal portion 130*df* inverts as shown. In the specific embodiment shown, the free distal portion 130*df* inverts to forms a partial conical structure having an origin $O_{d2}$ (shown by intersection of imaginary dashed lines) that lies proximal to the free distal portion 130*df*, in particular, the free distal portion 130*df* comprises a frustum of a cone having an origin $O_{d2}$ that lies proximal to the frustum. Angle $\alpha_{d2}$ is the angle between the longitudinal axis $A_l$ and the surface of the partial conical structure. Values for $\alpha_{d2}$ typically range between the value of $\alpha_p$ and 90°. The diameter D of the of the structure will vary, depending, for example, on the size of the vessel into which the catheter is to be inserted, ranging, for example, from 2.5 mm to 100 mm, for instance, ranging from 3 mm to 5 mm to 10 mm to 25 mm to 50 mm to 100 mm (i.e., ranging between any two of the preceding numerical values). Where the vessel is a hepatic artery, the diameter D may range from 4 mm to 8 mm, more typically ranging from 5 mm to 7 mm, or about 6 mm.

As previously indicated, engagement of the flexible structure 130 with a wall of a surrounding fluid vessel upon adopting the profile shown creates a check valve for fluid flowing in the fluid vessel. In particular, a check valve is formed wherein fluid flow in a distal-to-proximal direction is at least substantially blocked relative to fluid flow in a proximal-to-distal direction, because the flexible structure 130 is more resistant to deformation due to fluid pressure in a proximal direction than it is to deformation due to fluid pressure in a distal direction. Such a device may be used, for example, to inhibit retrograde flow while minimizing the effect of the device on natural blood flow (e.g., in conjunction with the delivery of embolics, other fluid therapeutics, contrast media, etc.)

In the embodiment shown in FIGS. 1A-1C, the flexible structure 130 is generally continuous. Because it is desirable in various embodiments to at least partially invert the distal portion 130*d* and because it is undesirable to invert the proximal portion 130*p*, various measures may be taken to ensure that the free distal portion 130*df* more readily inverts than the free proximal portion 130*dp*.

For example, in some embodiments, the free distal portion 130*df* may be made of thinner material than the free proximal portion 130*dp*.

Figure 2:
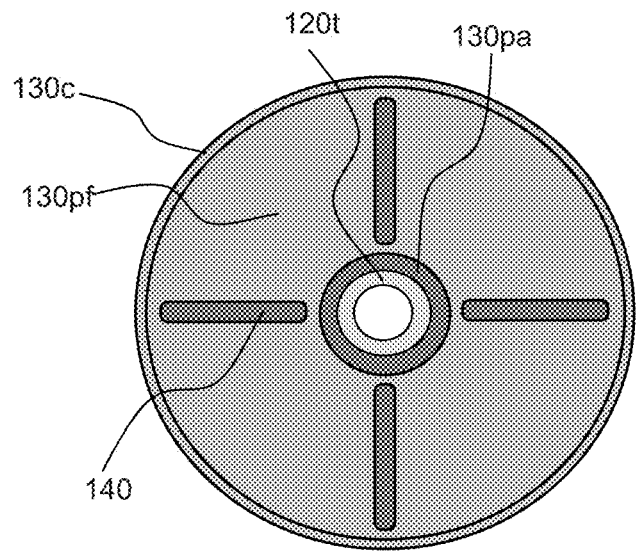
FIG. 2 is a schematic proximal end view of a proximal end of catheter in accordance with an embodiment of the present disclosure.

In some embodiments, the free proximal portion 130*pf* may be reinforced, for example, with a plurality of longitudinal reinforcement members 140 along the free proximal portion 130*pf*, for instance, as shown in FIG. 2, which is a schematic end view (from the proximal end) of portion of a device similar in construction and orientation to that of FIG. 1B. The longitudinal reinforcement members 140 may be provided on an exterior surface (as shown), interior surface or within a wall of the free proximal portion 130*pf*. While four longitudinal reinforcement members 140 are shown in FIG. 2, more or less longitudinal reinforcement members may be employed in various other embodiments.

Figure 3:
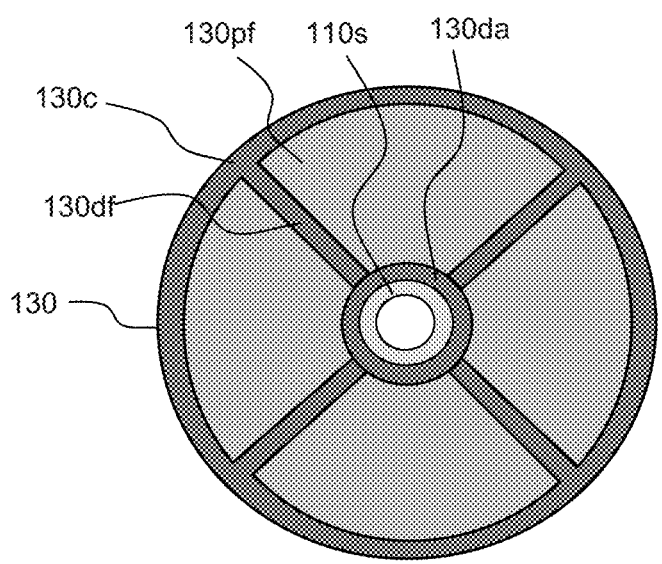
FIG. 3 is a schematic distal end view of a catheter in accordance with an embodiment of the present disclosure.

In some embodiments, the free distal portion 130*df* may be in the form of a discontinuous piece of material. For example, FIG. 3 shows a schematic end view (from the distal end) of portion of a device similar in construction and orientation to that of FIG. 1B, except that a plurality of (specifically, four) substantially pie shaped apertures have been formed in the free distal portion 130*df*, such that the free distal portion 130*df* comprises a plurality of (specifically, four) thin elongated members. By cutting a substantial amount of material out of the free distal portion 130*df*, the free distal portion 130*df* is rendered more flexible and thus more readily inverts that the proximal portion 130*p*. While four windows are cut in the free distal portion 130*df* of FIG. 3, more or less widows of similar or different shape may be employed in various other embodiments.

A variety of organic (e.g., polymeric) and inorganic (e.g., metallic) materials may be used to form the elongate members (e.g., outer tube, inner tube, and stop member) described herein. In certain embodiments, the inner and outer tubular members may be formed, for example, from a tube of polymeric material such as polytetrafluoroethylene (PTFE), polyether block amide (e.g., PEBAX), a tube formed from a coiled filament formed from a suitable polymer or a metal (e.g., stainless steel, titanium, etc.), or any other suitable flexible tubular material. The stop member may be formed from similar materials.

A variety of organic (e.g., polymeric) and inorganic (e.g., metallic) materials may also be used to form flexible structures for use in conjunction with the present disclosure. Suitable polymers may be selected from elastomers such as alkylsiloxane polymers (e.g., polydimethylsiloxane, also known as silicone rubber), polyurethane, or a styrene-isobutylene copolymers such as polystyrene-polyisobutylene-polystyrene triblock copolymer (SIBS), among others. In certain embodiments, a thermoplastic elastomer is selected. In certain embodiments, the flexible structure is formed using a molding technique such as injection molding or blow molding, among others.

The thickness of the flexible structure may vary depending on various factors including material used to form the flexible structure, and the diameter of the flexible structure when deployed, among other factors.

In certain embodiments, catheters in accordance with the present disclosure may be used to introduce therapeutic agents, including embolic agents, anti-cancer drugs and contrast media, into a hepatic artery, in which case the deployed diameter of the flexible structure may range from 4-8 mm, more typically ranging from 5-7 mm, or about 6 mm. In such embodiments, for an elastomeric polymer material such as silicone, the thickness of the flexible structure may range, for example, from 0.0025" to 0.0075" (0.06 mm to 0.19 mm), more typically from 0.004" to 0.006" (0.10 mm to 0.15 mm), or about 0.005" (0.13 mm).

Although various embodiments are specifically illustrated and described herein, it will be appreciated that modifications and variations of the present disclosure are covered by the above teachings and are within the purview of the appended claims without departing from the spirit and intended scope of the invention.

What is claimed is:

1. A device configured for insertion in a lumen, said device comprising:
   (a) an outer elongated member,
   (b) an inner elongated member disposed within the outer elongated member and axially movable with respect to the outer elongated member,
   (c) a stop member disposed about the inner elongated member and axially movable with respect to the outer elongated member, and
   (d) a flexible structure having a distal portion attached to the stop member and a proximal portion attached to the outer elongated member and configured such that when the inner elongated member is extended distally relative to the outer elongated member, the flexible structure adopts a reduced width profile and such that when the inner elongated member is retracted proximally relative to the outer elongated member to a point of maximal retraction, the flexible structure adopts an expanded width profile with a first frustum having a first frustum angle substantially within a second frustum having a second frustum angle that is smaller than the first frustum angle, the expanded width profile being more resistant to deformation due to fluid pressure in a proximal direction than it is to deformation due to fluid pressure in a distal direction.

2. The device of claim 1, wherein the stop member is configured to establish the point of maximal retraction.

3. The device of claim 1, wherein a resting shape of the flexible structure has a width that increases from a proximal end of the flexible structure towards a center of the flexible structure.

4. The device of claim 1, wherein a resting shape of the flexible structure comprises a first partial conical or partial pyramidal structure which has a width that increases from a proximal end of the flexible structure toward a center of the flexible structure.

5. The device of claim 1, wherein the proximal portion comprises a free proximal portion and an attached proximal portion that is attached to the outer elongated member, and wherein the distal portion comprises a free distal portion and an attached distal portion that is attached to the stop member.

6. The device of claim 5, wherein when the inner elongated member is at the point of maximal retraction, the free proximal portion has a width that increases in a proximal-to-distal direction.

7. The device of claim 5, wherein when the inner elongated member is at the point of maximal retraction, the free proximal portion comprises a first partial conical or partial pyramidal structure which has a width that increases in a proximal-to-distal direction.

8. The device of claim 7, wherein a resting shape of the flexible structure is such that the free distal portion comprises a second partial conical or partial pyramidal structure which has a width that increases in a distal-to-proximal direction.

9. The device of claim 8, wherein upon retraction of the inner elongated member proximally relative to the outer elongated member, the second partial conical or partial pyramidal structure at least partially inverts and at least partially nests within the first partial conical or partial pyramidal structure.

10. The device of claim 7, wherein the free proximal portion comprises the second frustum.

11. The device of claim 10, wherein the free distal portion comprises the first frustum.

12. The device of claim 11, wherein the flexible structure has a resting shape in which a width of the proximal portion increases in a proximal-to-distal direction and in which a width of the distal portion increases in a distal-to-proximal direction.

13. The device of claim 11, wherein when the inner elongated member is retracted to the point of maximal retraction, the first frustum has a configuration in which a width of the first frustum increases in a proximal-to-distal direction.

14. The device of claim 11, wherein the first frustum is provided with a plurality of apertures.

15. The device of claim 14, wherein the apertures form a plurality of elongated members that are positioned between the attached distal portion and the free proximal portion.

16. The device of claim 11, wherein the first frustum is thinner than the second frustum thereby rendering the first frustum more flexible than the second frustum.

17. The device of claim 1, wherein the device is a catheter.

18. A method comprising:
   (a) inserting a device into a lumen, the device comprising:
      (i) an outer elongated member,
      (ii) an inner elongated member disposed within the outer elongated member and axially movable with respect to the outer elongated member,
      (iii) a stop member disposed about the inner elongated member and axially movable with respect to the outer elongated member, and
      (iv) a flexible structure having a distal portion attached to the stop member and a proximal portion attached to the outer elongated member and configured such that when the inner elongated member is extended distally relative to the outer elongated member, the flexible structure adopts a reduced width profile and such that when the inner elongated member is retracted proximally relative to the outer elongated member to a point of maximal retraction, the flexible structure adopts an expanded width profile that is more resistant to deformation due to fluid pressure in a proximal direction than it is to deformation due to fluid pressure in a distal direction, said device being inserted into the lumen while the flexible structure is in the reduced width profile,
   (b) retracting the inner elongated member proximally relative to the outer elongated member to the point of maximal retraction, such that the flexible structure adopts the expanded width profile with a first frustum having a first frustum angle substantially within a second frustum having a second frustum angle that is smaller than the first frustum angle, the expanded width profile engaging an inner surface of the lumen and creating a check valve in which the expanded width profile is more resistant to deformation due to fluid pressure in the proximal direction than it is to deformation due to fluid pressure in the distal direction.

19. The method of claim 18, wherein the lumen is a blood vessel, wherein the device is a catheter, and wherein a therapeutic agent is delivered from the catheter at a point that is distal to the flexible structure.

20. A valve structure comprising:
a flexible structure having a distal portion configured for attachment to a stop member disposed about a first member, and a proximal portion configured for attachment to a second member, wherein the flexible structure is configured such that when the first member is extended distally relative to the second member, the flexible structure adopts a reduced width profile and such that when the first member is retracted proximally relative to the second member to a point of maximal retraction, the flexible structure adopts an expanded width profile with a first frustum having a first frustum angle substantially within a second frustum having a second frustum angle that is smaller than the first frustum angle, the expanded width profile being more resistant to deformation due to fluid pressure in a proximal direction than it is to deformation due to fluid pressure in a distal direction.

* * * * *